(12) United States Patent
Kampasi et al.

(10) Patent No.: US 10,695,581 B2
(45) Date of Patent: Jun. 30, 2020

(54) MULTICOLOR NEURAL OPTOELECTRODE

(71) Applicant: The Regents of the University of Michigan, Ann Arbor, MI (US)

(72) Inventors: Komal Kampasi, Ann Arbor, MI (US); Euisik Yoon, Ypsilanti, MI (US); John P. Seymour, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 653 days.

(21) Appl. No.: 15/185,209

(22) Filed: Jun. 17, 2016

(65) Prior Publication Data

US 2016/0367836 A1     Dec. 22, 2016

Related U.S. Application Data

(60) Provisional application No. 62/182,289, filed on Jun. 19, 2015.

(51) Int. Cl.
| | | |
|---|---|---|
| *A61B 5/00* | (2006.01) | |
| *A61N 5/06* | (2006.01) | |
| *G02B 6/42* | (2006.01) | |
| *F21V 8/00* | (2006.01) | |
| *A61N 5/067* | (2006.01) | |
| *A61N 5/00* | (2006.01) | |
| *G02B 6/12* | (2006.01) | |

(52) U.S. Cl.
CPC .......... *A61N 5/0622* (2013.01); *A61N 5/0601* (2013.01); *G02B 6/0008* (2013.01); *G02B 6/4204* (2013.01); *A61N 2005/005* (2013.01); *A61N 2005/063* (2013.01); *A61N 2005/067* (2013.01); *A61N 2005/0612* (2013.01); *A61N 2005/0651* (2013.01); *A61N 2005/0662* (2013.01); *G02B 6/4269* (2013.01); *G02B 2006/12147* (2013.01)

(58) Field of Classification Search
CPC .. A61B 5/0066; A61B 5/6852; G01B 9/02091
See application file for complete search history.

(56) References Cited

U.S. PATENT DOCUMENTS

| | | | | |
|---|---|---|---|---|
| 6,201,989 | B1* | 3/2001 | Whitehead | A61B 5/0071 250/461.2 |
| 6,485,413 | B1* | 11/2002 | Boppart | A61B 1/00096 356/450 |
| 8,870,857 | B2 | 10/2014 | Seymour et al. | |
| 9,814,390 | B2* | 11/2017 | Piron | A61B 90/39 |
| 2014/0180133 | A1* | 6/2014 | Brennan | A61B 1/00096 600/478 |

* cited by examiner

*Primary Examiner* — Michael J D Abreu

(74) *Attorney, Agent, or Firm* — Reising Ethington P.C.

(57) ABSTRACT

An optoelectrode having a lens optically coupled between a light source and a light guide and a method of making an optoelectrode. In one embodiment of the optoelectrode, the lens is a gradient index (GRIN) lens and the light source is a side-emitting injection laser diode (ILD). The optoelectrodes can be implemented such that they are high density, highly compact, monolithically integrated, and can deliver multicolor light output independently and simultaneously at a common waveguide port using an optical mixer, for example. In a preferred embodiment, the optoelectrodes are used as neural probes.

18 Claims, 14 Drawing Sheets

MULTICOLOR NEURAL OPTOELECTRODE

TECHNICAL FIELD

This invention relates generally to optoelectrodes, and more particularly, to structures and methods relating to the manufacture of multicolor optoelectrodes.

BACKGROUND

Optogenetics is a relatively new technology in the field of neuroscience that combines genetic targeting of specific neurons or proteins with optical technology. Optogenetics is based on the genetic transfection of specific cell types to express photosensitive proteins, whose spiking activities can then be precisely controlled by light pulses of specific wavelengths. These light-responsive proteins, called opsins, are used to selectively turn neurons on or off with specificity and precise temporal resolution. Neurons now may be controlled with optogenetic tools for fast, specific excitation or inhibition within systems as complex as freely moving mammals. Probes are used to take advantage of genetic targeting strategies to express light-sensitive proteins in genetically defined populations of neurons, allowing unambiguous identification of the neurons under investigation. By using light-sensitive probes, it is possible to control the activity of entire populations of potential presynaptic neurons and/or monitor the responses of populations of potential postsynaptic neurons. Optogenetic tools can provide new ways to establish causal relationships between brain activity and behavior in health and disease. However, while the exploration of the wiring diagram of neural networks is moving forward at an unprecedented scale and steady innovations in optogenetics may provide a toolset for identifying and manipulating circuit components, innovative approaches that enable low-cost, practical solutions for optogenetic tools are lacking.

The development of reliable chronic brain implants that can access the activity of large populations of individual neurons with high spatial and temporal resolution is ongoing. Several groups have developed larger-scale optoelectrodes to deliver optical stimulation light to deep brain structures while simultaneously recording neurons. However, light sources placed on the surface of brain or large fibers placed in the brain parenchyma a few hundred microns away from the recording sites inevitably require excessive power to illuminate the large area of the brain and in turn, activate many untargeted neurons. A complete multi-color optical stimulation and electrical recording system was demonstrated using diode-coupled optical fibers attached to commercial multi-shank silicon probes. However, the manual attachment of fibers glued to portable light sources on probe shanks can be highly variable and labor-intensive. Recently, a monolithically integrated optical waveguide in a multi-electrode array silicon probe, precisely delivering light in the proximity of recording sites was developed. But in that case, the waveguide was connected to an on-bench solid-state laser source through optical fibers. Direct assembly of light sources on the silicon probe back-end was also introduced, but the issue of potential device heating, which can cause thermal damage to the surrounding brain tissue during device operation, needs to be addressed. Providing light sources on the probe shank and/or using an optical fiber to transmit light from the probe back-end to the optical emission port on the probe can lead to undesirable heating of the target site, and possibly tissue damage. Further, a reliable coupling scheme should be optimized for efficient optical coupling between the light source and the waveguide. Thus, while the exploration of optoelectrodes is moving ahead with advances in MEMS, microelectronics and optics, innovative approaches that enable practical solutions for multiple wavelength optogenetic tools for precise neural circuit manipulation are lacking.

SUMMARY

According to one embodiment, there is provided an optoelectrode comprising a probe shank, a light guide positioned on the probe shank, a source module, a light source attached to the source module, and a lens. The lens is optically coupled between the light source and the light guide such that light from the light source can be directed by the lens to the light guide and transmitted through the light guide to an optical emission port of the probe shank.

According to another embodiment, there is provided an optoelectrode comprising a waveguide ending at an optical emission port configured to be inserted into a tissue sample, a light source, and a gradient index (GRIN) lens. The GRIN lens is optically coupled between the light source and the waveguide such that light from the light source can be directed by the lens to the waveguide and transmitted through the waveguide to the optical emission port.

According to another embodiment, there is provided a method of making an optoelectrode. The method comprises the steps of assembling a light guide on a probe shank, assembling a light source on a source module, and coupling the light source to the light guide using a lens.

BRIEF DESCRIPTION OF THE DRAWINGS

Preferred exemplary embodiments will hereinafter be described in conjunction with the appended drawings, wherein like designations denote like elements, and wherein.

DESCRIPTION OF THE ILLUSTRATED EMBODIMENTS

As described below, a fiberless optoelectrode can be constructed that can selectively target individual neurons or groups of neurons with light of different wavelengths, while minimizing undesirable heating of the targeted tissue from the light source. The optoelectrodes described herein are highly compact, monolithically integrated, and can deliver multicolor light output alternatively at a common waveguide port using an optical mixer, for example. In one embodiment, the optoelectrode is implemented using an efficient end-fire coupling between a side-emitting injection laser diode (ILD) chip and a monolithically integrated dielectric waveguide via a gradient index (GRIN) lens onto a neural probe. The use of a GRIN lens may afford several advantages over other conventional approaches for smaller-scale optogenetic tool designs. More specifically, the GRIN lens may provide thermal isolation between the light source and the waveguide, thereby prolonging the total continuous operational time of the optoelectrode by at least ten-fold in some embodiments. The use of a GRIN lens may also simplify manufacturing because it provides improved tolerance and alignment when coupling a light source with a waveguide. Accordingly, an optoelectrode as described herein can enable independent activation and silencing of precise neural circuits at a common light port, thus allowing neuroscientists to study nervous system activity with unmatched spatial precision and scalability. In one example, the optoelectrode provides for both violet/blue (e.g., excitation) as well as yellow/red (e.g., inhibition) stimulatory illumination. The optoelectrode embodiments and manufacturing methods detailed below can simplify packaging, improve noise immunity, and minimize heat conduction to the end of the probe tip, thereby preventing possible tissue heating when high illumination light sources are used. While preferred embodiments of the optoelectrode are both fiberless and multicolor, it should be understood that one or more embodiments may include an optical fiber or may only have one color of light. Also, while the optoelectrode is preferably used as a neural probe, other applications and implementations are certainly possible.

Figure 1:
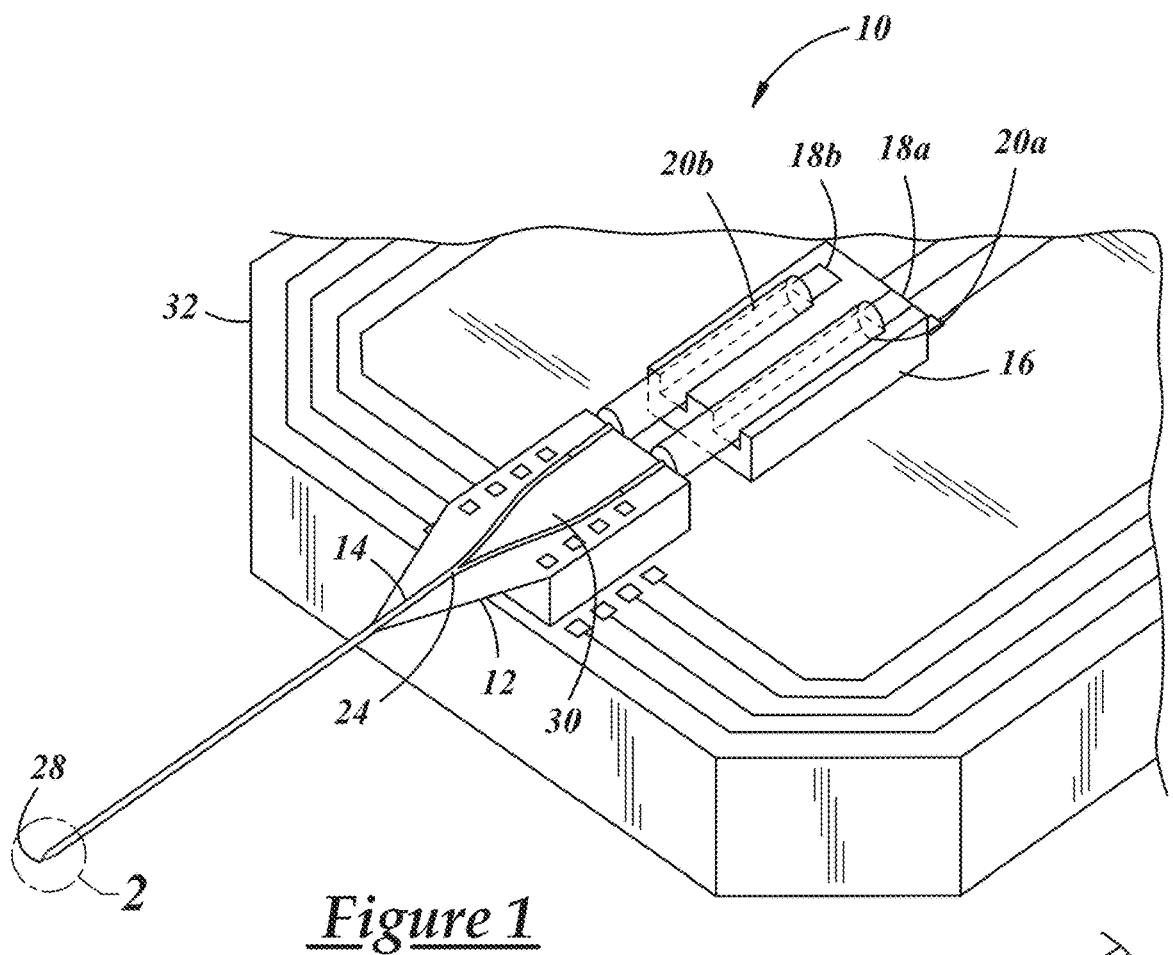
FIG. 1 is a perspective view of one embodiment of a fiberless multicolor optoelectrode.
Figure 2:
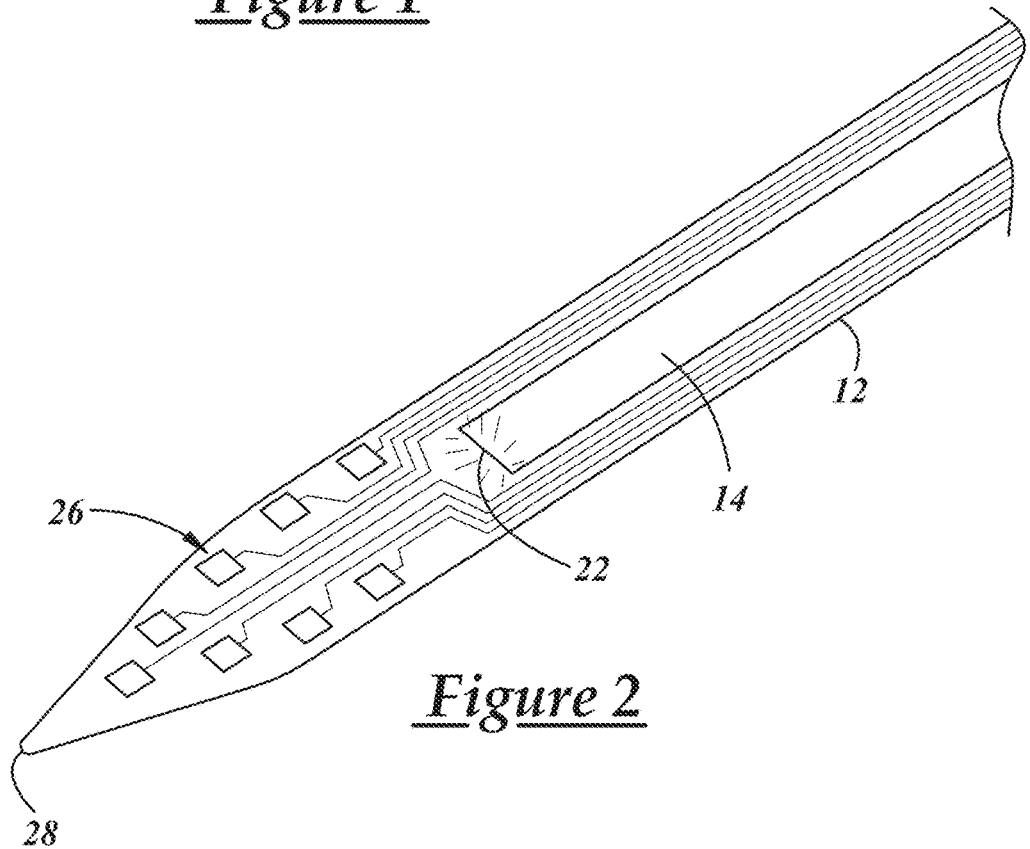
FIG. 2 is an enlarged view of the tip portion of the optoelectrode of FIG. 1.
Figure 3:
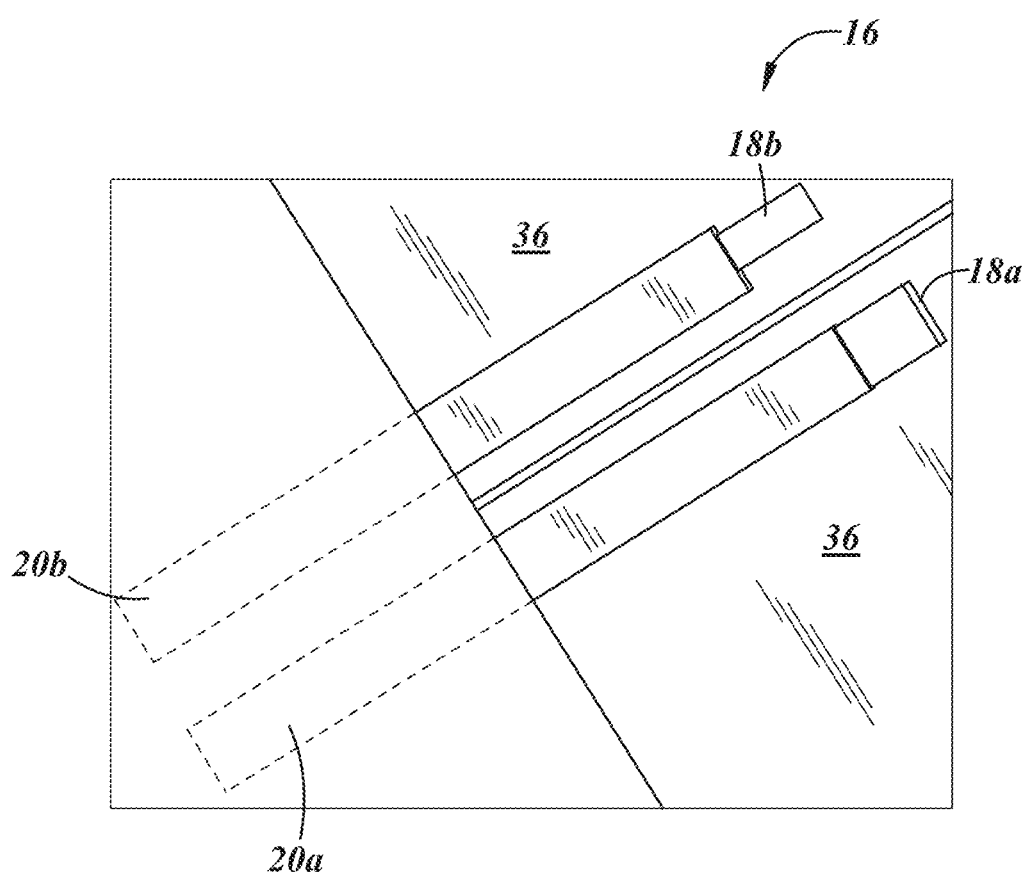
FIG. 3 is an enlarged view of a source module of the optoelectrode of FIG. 1.

With reference to FIGS. 1-4, there is shown an optoelectrode 10 and some of its components. As shown in FIG. 1, the optoelectrode includes a probe shank 12 and a light guide 14 positioned on the probe shank. In the illustrated embodiments, the light guide is a waveguide, but it may be possible to include other types of light guides such as an optical fiber or the like. FIG. 2 shows an enlarged view of a tip 28 of the probe shank 12. The optoelectrode 10 further includes a source module 16. The source module may be a separate component or stage as shown, or it may be a non-distinct part of the probe body or another component of the device, to cite just a few examples. Any operable component used to house or otherwise hold one or more light sources and/or optical lenses may be considered a source module. FIG. 3 shows a source module 16 which may include or comprise a heat sink 36. The heat sink may be the source module itself or another component attached to or housed with the source module. The optoelectrode 10 includes two light sources 18a, 18b that are attached to or otherwise housed with the source module 16. The separate source module 16 can help with thermal isolation and result in less electrical interference (e.g., low-artifacts) between electrical traces of a fiberless light source and electrode recording channels on the probe shank 12. The illustrated embodiment includes two lenses 20a, 20b which optically couple the light sources 18a, 18b to the waveguide 14 so that light from the light sources can be transmitted through the waveguide to an optical emission port 22 of the probe shank 12. The waveguide in this embodiment includes an optical mixer 24 that can facilitate the selective transmission of light from each light source 18a, 18b such that a different color light may be emitted at a single port. There may be more waveguide ports designed along the entire length of the waveguide, other than at the proximal end port 22. Returning to FIG. 2, in electrode array 26, containing one or more electrodes, may be included to record neural stimulation. The electrode array 26 is a Buzsaki 8-electrode configuration at the probe shank tip 28 which is opposite the probe back-end 30. There may be more or less electrodes than what is illustrated in FIG. 2, and one or more electrodes may be situated at different points along the probe shank, other than merely at the probe shank tip 28. One or more optoelectrode components may be mounted to a printed circuit board 32.

In a preferred embodiment, the light source 18 is an injection laser diode (ILD), and more particularly, a side-emitting ILD, and the lens 20 is a gradient-index (GRIN) lens. Light guide 14 can be a monolithic waveguide patterned on a probe shank 12 and is optically coupled to the light source 18 using the GRIN lens 20. While the light guide in the illustrated embodiments is shown as a waveguide 14, other types of light guides are certainly possible such as an optical fiber. Additionally, it should be understood that the lens may include any light coupling medium including but not limited to an optical lens (e.g., GRIN, spherical, ball, etc.) or a micro-fabricated beam focusing/coupling module (e.g., polymer lenses, gratings, optical switches, etc.) that are coupled between the light source and the light guide. Other types of lenses or a combination of more than one lens and/or lens type may be used. The GRIN lens is advantageous because it can collimate and focus an in-coupled divergent laser beam. It has flat coupling ends to facilitate efficient parallel end-butt coupling and simple packaging. Moreover, the GRIN lens can provide good thermal isolation between the light source and the silicon probe. The GRIN characteristics such as numerical aperture (N.A.), working distances, and magnification can be designed and optimized for device specifications, as shown in Table 1 below, where $\sqrt{A}$ is the lens gradient constant (mm$^{-1}$) which depends on material and wavelength; $N_0$ is the refractive index (RI) at the lens central axis (1.65); P is the lens pitch, which is a fraction of a full sinusoidal period of the ray path; $n_o$ is the RI of the surrounding medium around the GRIN lens; $\theta_a$ is the lens acceptance angle) (25°); and L1 is the object distance.

TABLE 1

| GRIN Parameter | Equation |
| --- | --- |
| Length, Z | $2\pi P/\sqrt{A}$ |
| Refractive index at radial distance r, N | $N_0(1 - (A/2)r^2)$ |
| Numerical aperture, N.A. | $n_o \sin\theta_a$ |

Figure 4:
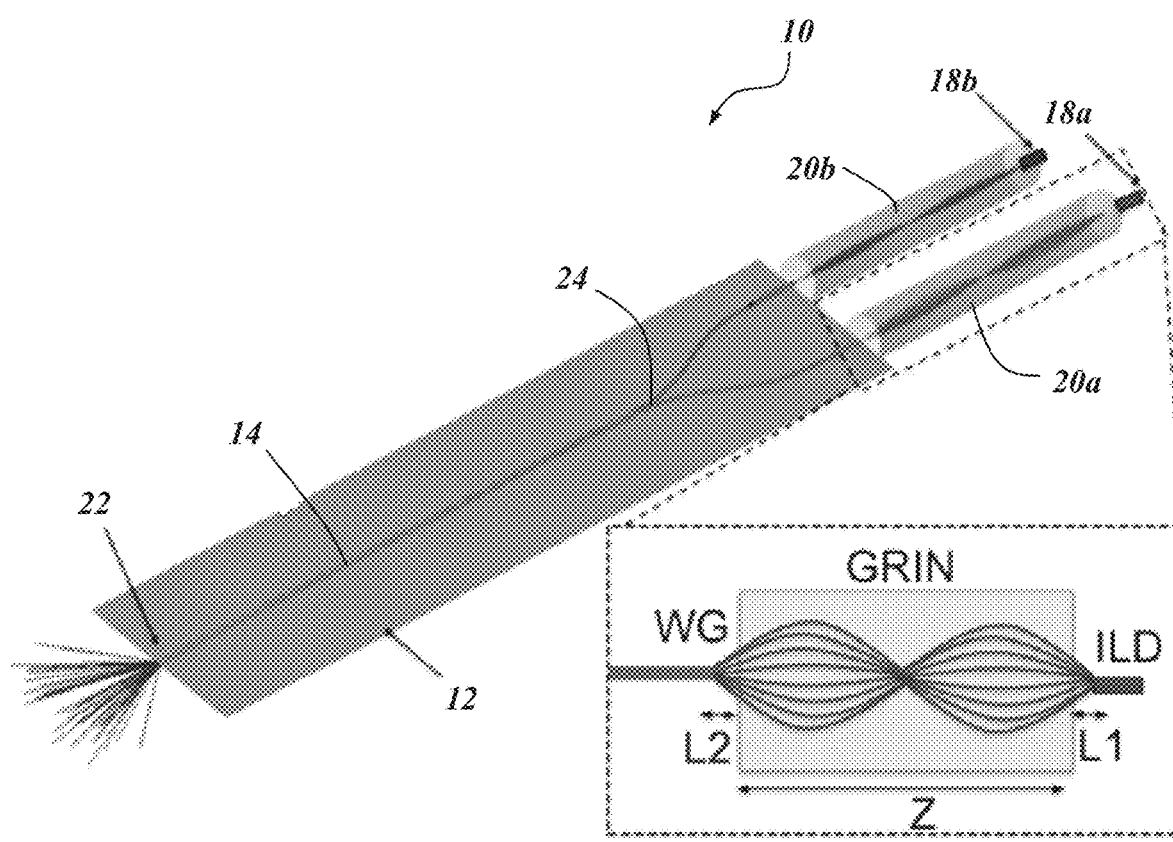
FIG. 4 illustrates optical ray tracing model of one embodiment of fiberless multicolor optoelectrode, comprising of ILDs, full-pitch gradient-index (GRIN) lenses and a waveguide mixer.

As shown in FIG. 4, a GRIN lens can provide an efficient coupling mechanism by sequential collimation and focusing of light rays within the lens. In a particular embodiment, a full pitch GRIN lens of N.A. equal to 0.4 was chosen. A full pitch GRIN lens gives a focused beam at the GRIN lens output because a beam travels exactly the full cycle of a sinusoidal period in that distance to achieve beam focusing on the other end. GRIN lens parameters, such as working distances (L1, L2) and mechanical length (Z), were optimized, as shown in Table 1, to match the aspect ratio of the device design.

It is advantageous in some embodiments for the waveguide to have an N.A. equal to or higher than the N.A. of the GRIN lens. This may lead to more efficient coupling of the GRIN lens to the waveguide. In such an embodiment, all incoming rays from the GRIN lens can be efficiently collected by the waveguide if aligned properly, and the losses occurring at the coupling interface are limited to reflection (Fresnel) losses. Fresnel losses are given by the equation $$F_L = (n_2 - n_1/n_2 + n_1)^2$$

where $n_1$ and $n_2$ are the RIs of the first and second media, respectively. In one implementation, the waveguide N.A. is 0.4228 (designed to closely match the NA of the GRIN lens, 0.4226) using the equation $$NA_{wg} = \sqrt{(n_{core}^2 - n_{clad}^2)}$$

where $n_{core}$ is the RI of the waveguide core (silicon oxynitride, 1.52) and $n_{clad}$ is the RI of the waveguide cladding (silicon dioxide, 1.46). Using the Fresnel equation, reflective losses were calculated as 0.462 dB at the ILD-GRIN junction (assuming an intermediate medium with RI=1.56) and 0.463 dB at the GRIN-waveguide junction, yielding a total coupling loss of 0.925 dB (in this example, greater than 80% total coupling efficiency from the ILD to the waveguide).

The design of the optoelectrode may be tailored to specific experimental needs, and varied based on analytical optical equations. A parametric ray trace model can be developed to explore the design space in full depth, Zemax ray trace models may be used for design purposes. FIG. 4 illustrates an optical system model, which consists of two ILDs 18a, 18b (635 nm and 405 nm, respectively), coupled to the two arms of a 2 mm-long optically optimized mixer 24 via their respective GRIN lenses 20a, 20b. The mixer arms are tapered down from a width of 50 μm to 30 μm and finally coupled to a 5 mm-long straight waveguide 14 with a 30 μm×7 μm cross-section. The mixer geometry was optimized using analytical equations for dielectric optical bend waveguides to minimize radiation losses and mode conversion losses. The schematic in the inset shows a full pitch GRIN lens collimating and focusing a divergent ILD laser beam into the waveguide mixer arm (WG). L1 and L2 denote object and image distances, respectively, that can fit well within the device fabrication and assembly precision, in at least some embodiments. The length of the GRIN lenses can correspond with the wavelength of light from its associated ILD, as illustrated in FIGS. 1, 3 and 4. As shown, the GRIN lens 20a is proportionally longer for the ILD 18a which produces light having a longer wavelength, and the GRIN lens 20b is proportionally shorter for the ILD 18b which produces light having a shorter wavelength. The optical transmission properties of the optoelectrode 10 were quantified by determining optical loss in multiple parts of the system, such as (1) coupling losses at the ILD-GRIN and GRIN-waveguide interfaces (coupling joints); (2) radiation loss in the bends of the optical mixer; and (3) scattering and absorption losses through the waveguide.

In a preferred embodiment, side emitting ILDs, such as light sources 18a, 18b shown in FIG. 3, are attached to the source module 16 in an epi-down configuration. To achieve the epi-down bonding, In—Au eutectic bonding at 200° C. may be used. With an epi-down configuration, the diode is flip-chipped with anode side facing down, so that the proximity of the heated active region is close to a heat sink 16. The ILD cathodes may be grounded to the ground plane of the PCB, and in one embodiment, they can be grounded via wirebonds and thermal conductive epoxy. This can allow for a more rapid heat dissipation from the active region to the heat sink. Indium was chosen for low-temperature diode bonding since it has a lower melting point of 156° C. (even lower than the melting temperature of tin, which is 232° C.), and it can enable void-free bond-joint formation with high thermal conduction during diode operation. Low-temperature indium-gold eutectic bonding can be used since it can protect the ILDs from potential thermal damage at high bonding temperatures. While an epi-down configuration is preferred, it is possible to use an epi-side up configuration as well for one or more of the light sources.

After flip-chipping the ILDs 18a, 18b to achieve an epi-down configuration, GRIN lenses 20a, 20b can be placed in a groove positioned in front of the ILDs, such that one end of each lens faces towards the corresponding ILD emission point and another end of each lens faces towards distal end of the optical mixer waveguide. The light output from the ILD-GRIN assembly was directed and focused into the input arms of the waveguide mixer on the silicon probe shank. The optical coupling junctions can be secured with a drop of index-matching epoxy, for example, to reduce Fresnel losses at the interfaces. In the illustrated embodiments, fabrication techniques and assembly setups were characterized to maximize alignment tolerance and minimize angle deviations. It should be understood that the light source 20 may include a laser diode (e.g., side-emitting, vertical-cavity surface-emitting (VCSEL), etc.), a light emitting diode (LED), or a fibered source, to cite a few examples.

As shown in FIG. 4, the focused beam can enter the tapered waveguide mixer arms of the optical mixer 24 and then into the straight waveguide 14. Due to optical mode distortion, radiation losses can occur in the waveguide bends. These losses can be minimized by designing the bend with a large radius of curvature. However, large curvature comes at the cost of a longer light path, resulting in higher transmission losses and larger device size, which is often limited by the maximum tolerance of pitch for micro-optical assemblies (e.g., limited by the diameter of the GRIN lenses). Due to this tradeoff, the mixer 24 was implemented with a maximum bend radius of 2.32 mm in a preferred embodiment while maintaining a minimum pitch between GRIN lenses. Such an implementation achieved simulated radiation loss within 1 dB. Other than coupling and radiation loss, light rays also suffer from as propagation loss, which is attenuation in the form of scattering and absorption as they travel through the guide. The total optical loss of the system, $L_T$, is typically the sum of all three loss-types, as provided in the following equation:

$$L_T(dB) = L_{coupling}(dB) + L_{propagation}(dB) + L_{radiation}(dB)$$

In a preferred embodiment, the coupling between the light source 18 and the GRIN lens 20 is an end-fire coupling. The coupling efficiency between a divergent laser beam and a step-graded waveguide, such as waveguide 14, can be significantly enhanced through the use of a collimation-focusing lens mechanism, or so called end-fire coupling. GRIN lenses are a preferred choice for the implementation of end-fire coupling. Since the lens performance can depend on a continuous change of the refractive index within the lens material, the light rays can be continuously bent within the lens until they are finally focused on one or more spots, as illustrated in FIG. 4. Flat optical end surfaces may be used for better coupling and the lenses can be made down to 250 μm in diameter. Such a simple geometry in a miniaturized size can allow for a very elegant optical coupling and assembly solution for microscale optoelectronic devices. In addition, the option of varying the lens length/pitch offers enormous flexibility when adjusting lens parameters, such as focal length and working distances, to meet desired design requirements.

Figure 5:
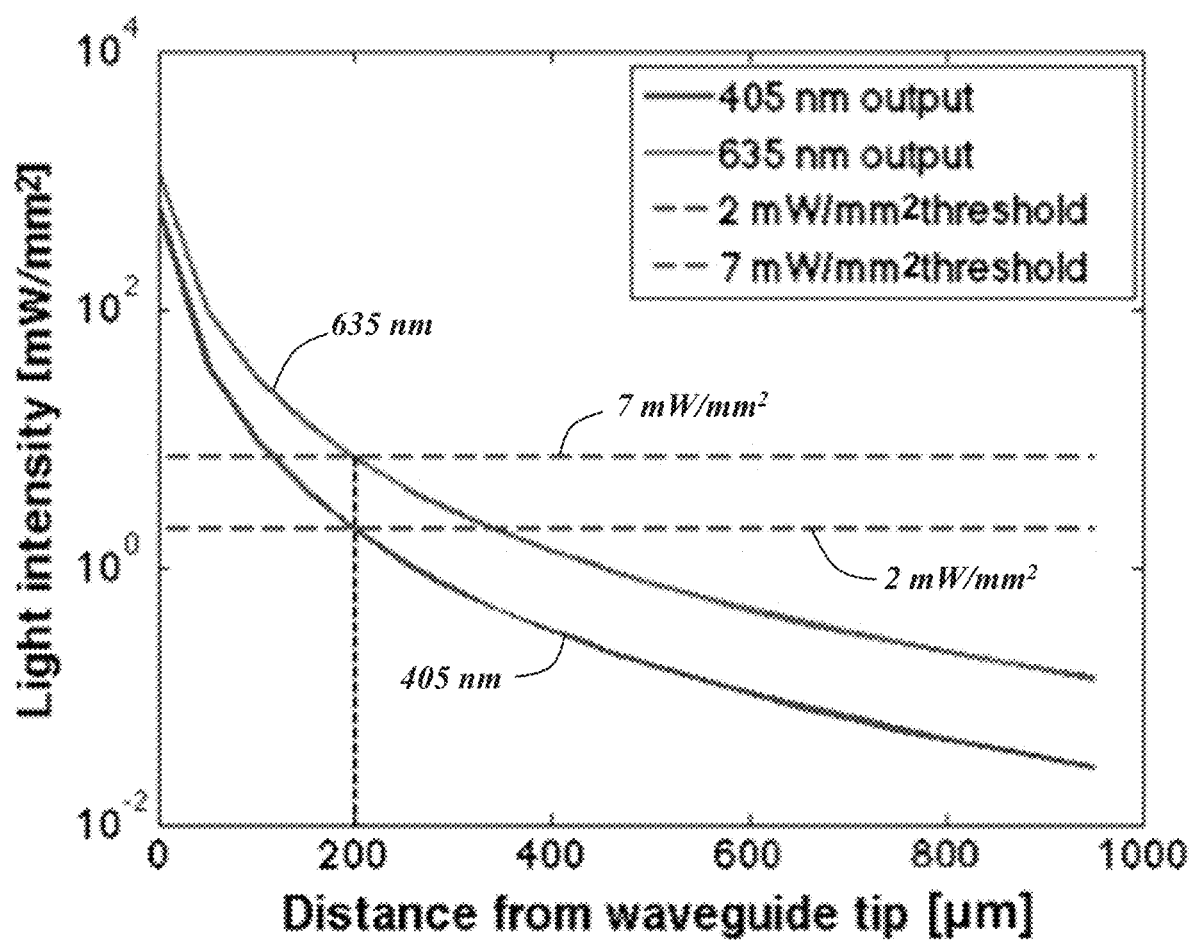
FIG. 5 is a graph showing the simulated light intensity inside brain tissue for the optoelectrode of FIG. 4.

In one embodiment, the waveguide aperture or the optical emitting site 22 on the shank 12 was positioned 55 μm away from the first recording site to minimize damage to the recorded neurons. Since the recording sites span 140 μm in this particular implementation, opsin activation thresholds must be crossed at a distance of ~200 μm from the tip of the of 7 μm×30 μm waveguide. The design values used in this example were: 405 nm light, intensity of 2 mW/mm$^2$ for ChR2; and 635 nm, intensity of 7 mW/mm$^2$ for Halo/Arch. Considering waveguide geometric losses and tissue scattering losses through tissue for each wavelength, the required light intensity is achieved at a distance of 200 μm from the waveguide if the output power (intensity) at the waveguide tip exceeds 100 μW (476 mW/mm$^2$) for 405 nm and 200 μW (952 mW/mm$^2$) for 635 nm. FIG. 5 shows these simulated light intensity curves at the optical emitting site 22 as a function of tissue depths. When output intensity at the waveguide tip is 476 mW/mm$^2$ for 405 nm and 952 mW/mm$^2$ for 635 nm, respectively, the tissue up to 200 μm away from the optical emitting port 22 can be illuminated at supra-threshold intensity.

The improved thermal properties of the optoelectrode 10 are illustrated in FIGS. 6-9. There are two considerations that should be addressed when designing an implantable optoelectrode. First, the temperature increase of the tissue should be considered. Although there is no established temperature threshold for safe operation of a probe when implanted in brain tissue in particular, temperature can impact neuronal activity on a cellular and population level in various manners. In this embodiment, a 1° C. temperature rise threshold from the baseline temperature of 37° C. is provided as a conservative thermal model analysis. Second, the temperature of the light source junction should be less than its thermal maximum, as higher temperatures can permanently damage light sources such as ILDs. In a preferred embodiment, ILDs with low optical power output (e.g., 5 mW) were chosen because of their high system efficiency. This efficiency may be important when scaling an optoelectrode system up to 8 or 16 independent light sources for multi-shank probes. Based on simulation results from a COMSOL Joule Heat Transfer model, at least 100 μW, or more preferably at least 200 μW, of optical power at 7×30 μm waveguide output should be generated to stimulate 200 μm of tissue in depth.

Figure 6:
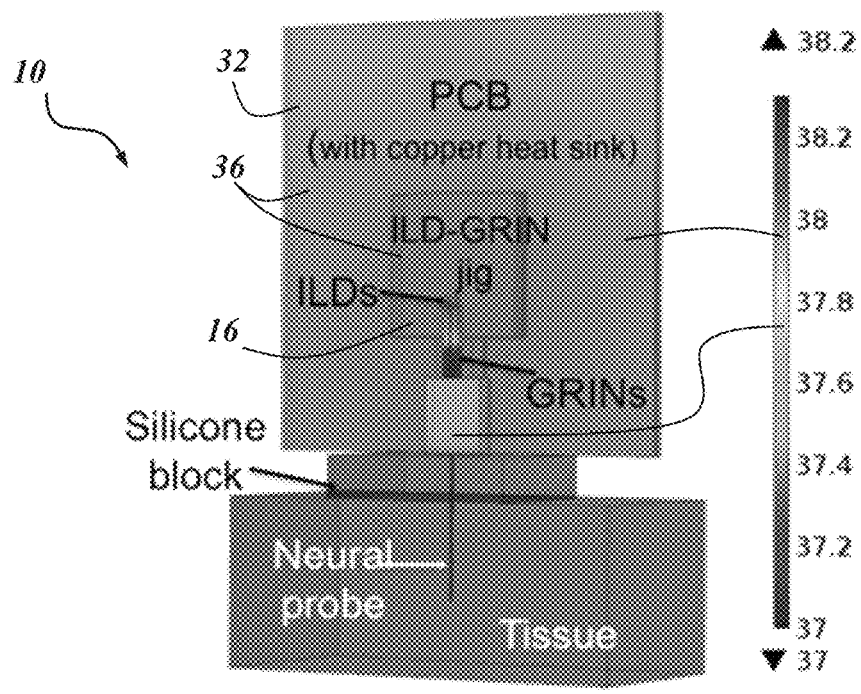
FIG. 6 is a COSMOL heat transfer model illustrating the potential temperature rise of optoelectrode components and the tissue surface when two GRIN-coupled ILDs are operated at 10% duty cycle power for 20 seconds.
Figure 7:
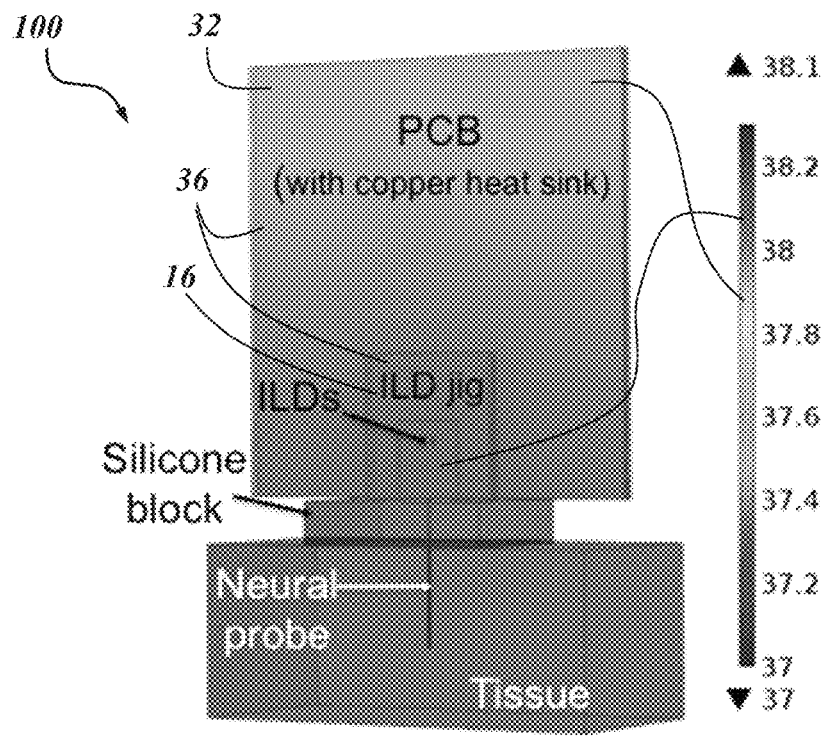
FIG. 7 is a COSMOL heat transfer model illustrating the potential temperature rise of optoelectrode components and the tissue surface when two butt-coupled ILDs are operated at 10% duty cycle power for 20 seconds.
Figure 8:
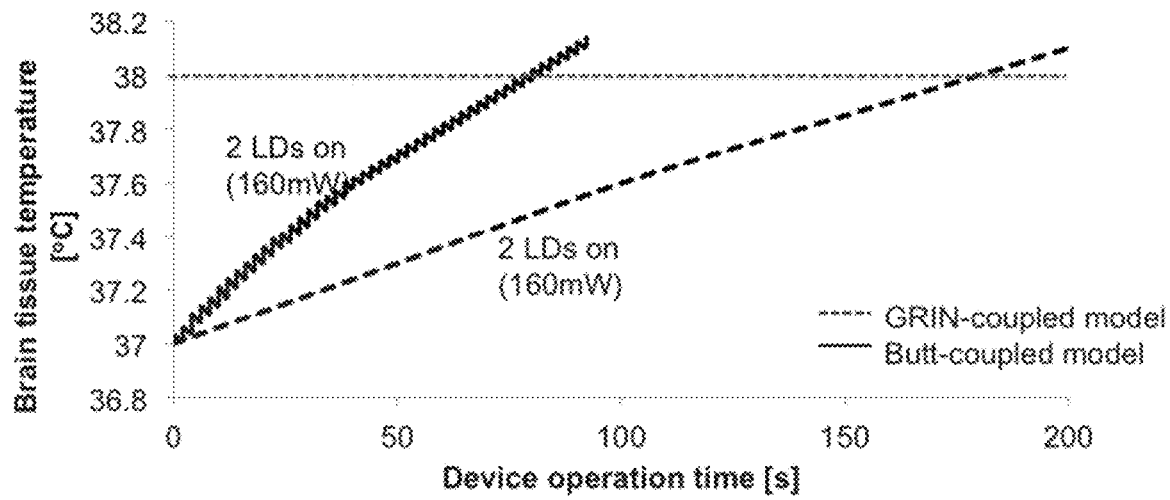
FIG. 8 is a graph illustrating the tissue temperature rise over time for the models shown in FIGS. 6 and 7.

FIGS. 6-8 illustrate the temperature rise of an optoelectrode 10 in accordance with one embodiment (FIG. 6), as compared with a butt-coupled optoelectrode 100 (FIG. 7). FIG. 6 is a COSMOL heat transfer model illustrating the potential temperature rise of optoelectrode components and the tissue surface when two GRIN-coupled ILDs are operated at 10% duty cycle power for 20 seconds. FIG. 7 is a COSMOL heat transfer model illustrating the potential temperature rise of optoelectrode components and the tissue surface when two butt-coupled ILDs are operated at 10% duty cycle power for 20 seconds. FIG. 8 is a graph illustrating the tissue temperature rise over time for the models shown in FIGS. 6 and 7. As addressed above, it is preferable to have power above 200 μW emitted at a 7×30 μm optical emitting site to achieve optogenetic activation in tissue as far as 200 μm away. Due to the high optical efficiency provided by the GRIN-based design, this can be achieved using low-power ILDs and driving them just above their stimulated emission threshold, at an input electrical power of ~80 mW in this particular embodiment. For conservative modeling, it was assumed that all electrical input power is dissipated as heat. The simulation results of FIGS. 6 and 8 indicate that both GRIN-coupled ILDs can be driven continuously for 190 sec just above their threshold current (200 msec pulse width, 10% duty cycle), which is more than adequate for most optogenetic circuit-analysis applications. The maximal temperature of the ILDs themselves (after 190 sec at 10% duty cycle) is 50.4° C. in this implementation, which is within the specified safe operational temperature. In an extreme case, when ILDs are driven by DC current, the continuous device operation time can be reduced to 45 sec, with a maximal ILD temperature of 52.4° C.

Figure 9:
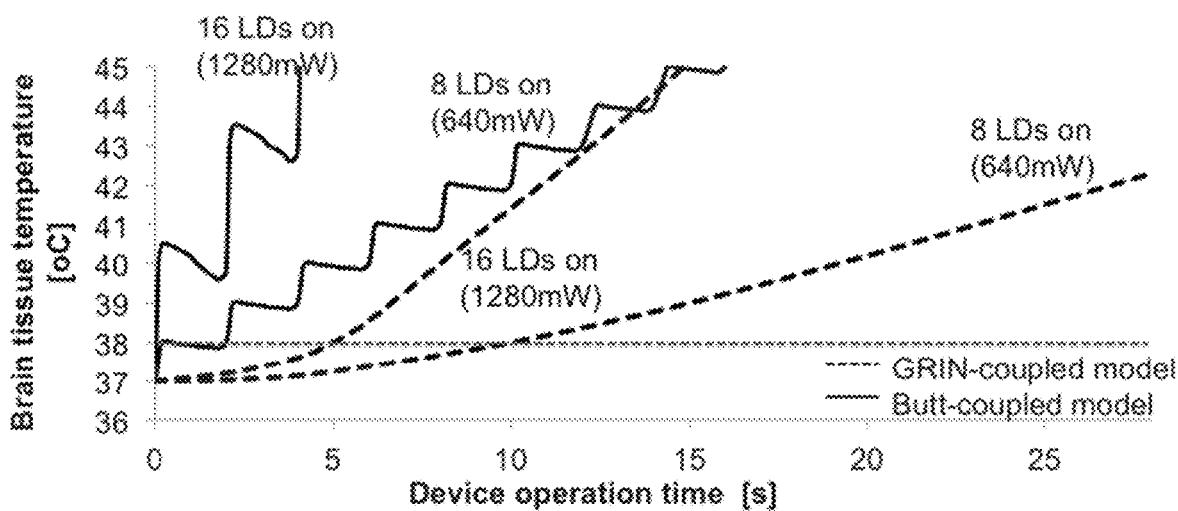
FIG. 9 is a graph illustrating tissue temperature rise over time for multi-shank GRIN-coupled optoelectrodes compared to their design equivalent butt-coupled optoelectrodes with 8 and 16 assembled diodes.

As shown in FIGS. 6 and 7, the GRIN-coupled design (FIG. 6) prolongs device operation time more than 2-fold as compared to a conventional design, in which diodes are directly butt-coupled to the waveguides without intermediate optical lenses (FIG. 7). This can influence the thermal budget when scaling the dual-ILD/single-shank device to multi-shank probes. As the number of diodes per device increases, the electrical power consumed increases, and hence the dissipated heat, increases. The temperature rise at the tissue surface for GRIN-coupled and butt-coupled designs, for 2-, 8- and 16-diode assemblies was also simulated, as shown in FIGS. 8 and 9. FIG. 9 is a graph illustrating tissue temperature rise over time for multi-shank GRIN-coupled optoelectrodes compared to their design equivalent butt-coupled optoelectrodes with 8 and 16 assembled diodes. The higher thermal resistance of the GRIN lenses can help manage the heat generated by the light sources without the use of active (e.g., thermoelectric) coolers. Instead, a heat sink 36, such as a copper heat sink surface on the PCB 32 or an indium/gold heat sink surface on the source module 16, may be attached to or otherwise integrated with one or more optoelectrode components to help in better heat dissipation. For example, the source module 16 may be further extended to become a larger heat sink or include an additional heat sink surface. Compared to the butt-coupled design where the rise in temperature is fast and oscillatory, the higher thermal constant offered by the GRIN-coupled design facilitates a slower and continuous temperature rise at the tissue, allowing future scaling in terms of the numbers of shanks and diodes.

There are also other advantages for using lasers as a light source 18. For example, they are highly compact, provide a directional beam with a wide power range, and are increasingly available in many wavelengths. In some embodiments, they may be preferred over LED-coupled systems, as it is possible to have poor coupling efficiency with LEDs because of their Lambertian light distribution profile. In a more particular embodiment, unpackaged side-emitting ILD chips are preferred over commercial ILD packages, as they can be incorporated into a fiberless, lightweight, microfabricated module that can enable precise assembly of optical components and facilitate the protection of electrical and thermal components of the device backend.

Figure 10:
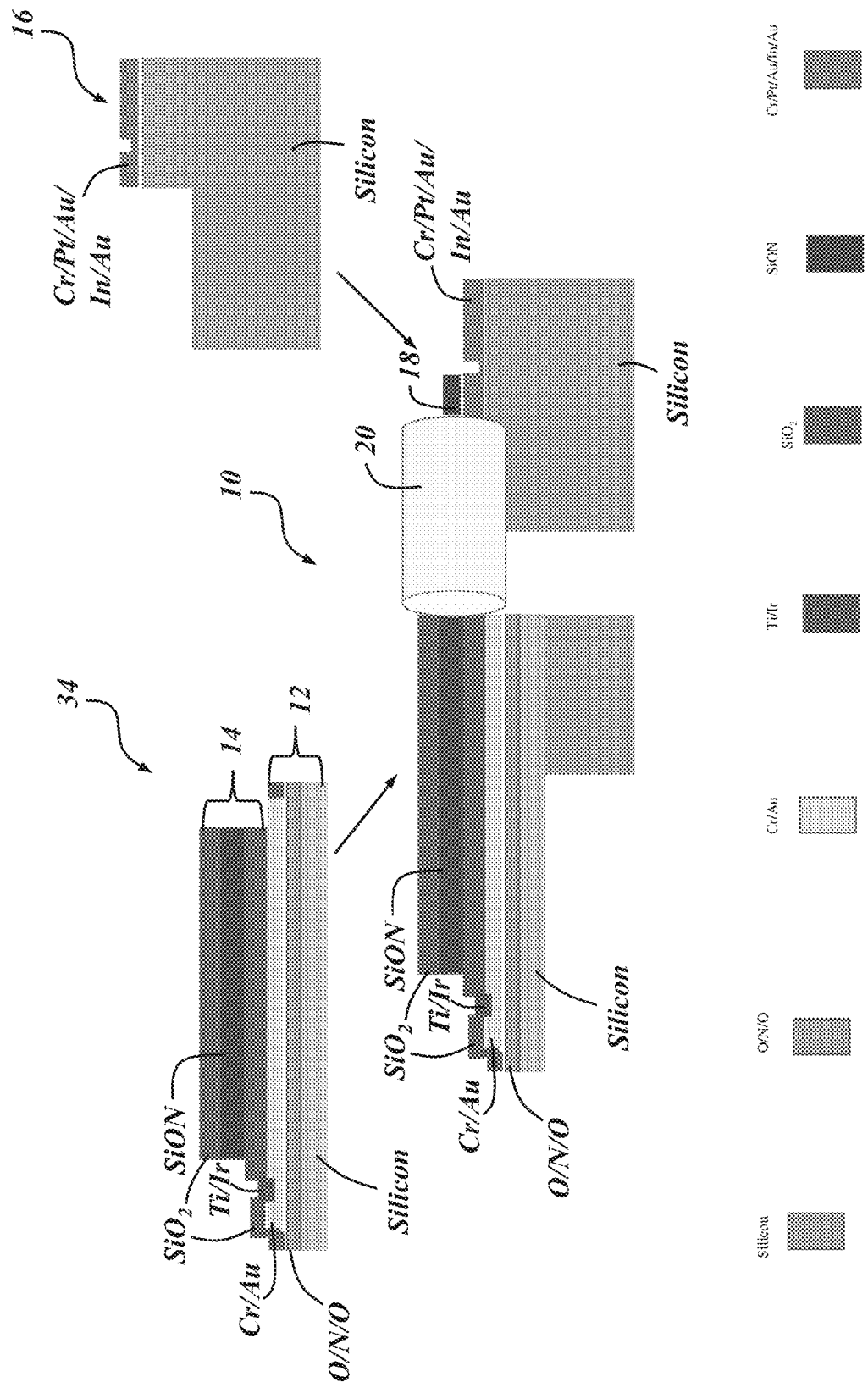
FIG. 10 illustrates fabrication steps of an optoelectrode in accordance with one embodiment.

A method of making an optoelectrode, such as optoelectrode 10, may include the steps of assembling a light guide on a probe shank, assembling a light source on a source module, and coupling the light source to the light guide using a lens. "Assembling" may include compiling various discrete components, fabricating or patterning one or more components, or any operable method of attaching, manufacturing, building, etc. In one embodiment, a waveguide is patterned on a probe shank and a lens is used to optically couple a light source to the waveguide. The waveguide fabrication is precise and may be customized. One exemplary fabrication process is illustrated in FIG. 10, where a waveguide 14 is integrated onto a 22 µm-thick neural probe shank 12 to form a monolithically integrated neural probe 34. The plasma-enhanced chemical vapor deposition (PECVD)-fabricated waveguide has a 7 µm-thick and 30 µm-wide a silicon oxynitride core (RI=1.52) with a 2 µm-thick silicon dioxide cladding (RI=1.46), achieving a waveguide N.A. of 0.42 in this particular example. The stress of dielectric waveguide films can be compensated for with an LPCVD-grown dielectric stack. Silicon oxynitride is an attractive material for use in optoelectrodes and for use in integrated biomedical optics in general. It possesses excellent optical properties and is resistant to saline and enzymatic environments, providing negligible in vivo degradation. It can be deposited with refractive indices varying over a wide range (1.45-2) by tuning the reaction gas compositions during deposition. Also, dielectric waveguides form an attractive solution for integrated biomedical optics. Unlike polymers, dielectrics are resistant to ionic and enzymatic environments, providing negligible in vivo degradation. In contrast to some polymer waveguides (e.g., SU-8, PDMS), dielectrics typically do not absorb light in the UV-blue range. Since the RI of the waveguide films determines the N.A. of the waveguide, the PECVD processes can be carefully optimized to tune the waveguide N.A. while maintaining film stress (e.g., 72 MPa tensile for silicon oxynitride and 180 MPa compressive for silicon dioxide, respectively) and uniformity (e.g., less than 1%) over the entire wafer surface. A 500 Å-thick aluminum oxide film was deposited under the waveguide films as an etch-stop, thereby avoiding potential damage to the metal surfaces underneath.

As addressed above, ILDs, and more particularly side-emitting ILDs, may be advantageously used for light sources 18. However, with ILDs, die bonding of the laser chip to the source module should be considered. ILDs can generate large heat fluxes that may adversely affect their performance and reliability, and thus a thermally effective packaging solution is desirable in order to remove excessive heat generated in the ILD to its surroundings as quickly and uniformly as possible. Thermal properties of laser diodes can have effects on many device characteristics, affecting wavelength, maximum output power, threshold current, slope efficiency, and operating lifetime, among other factors. Thus, development of ILD packaging is an important technological challenge for achieving high performance and may be an important step in some embodiments for reliable high yield production.

Figure 11:
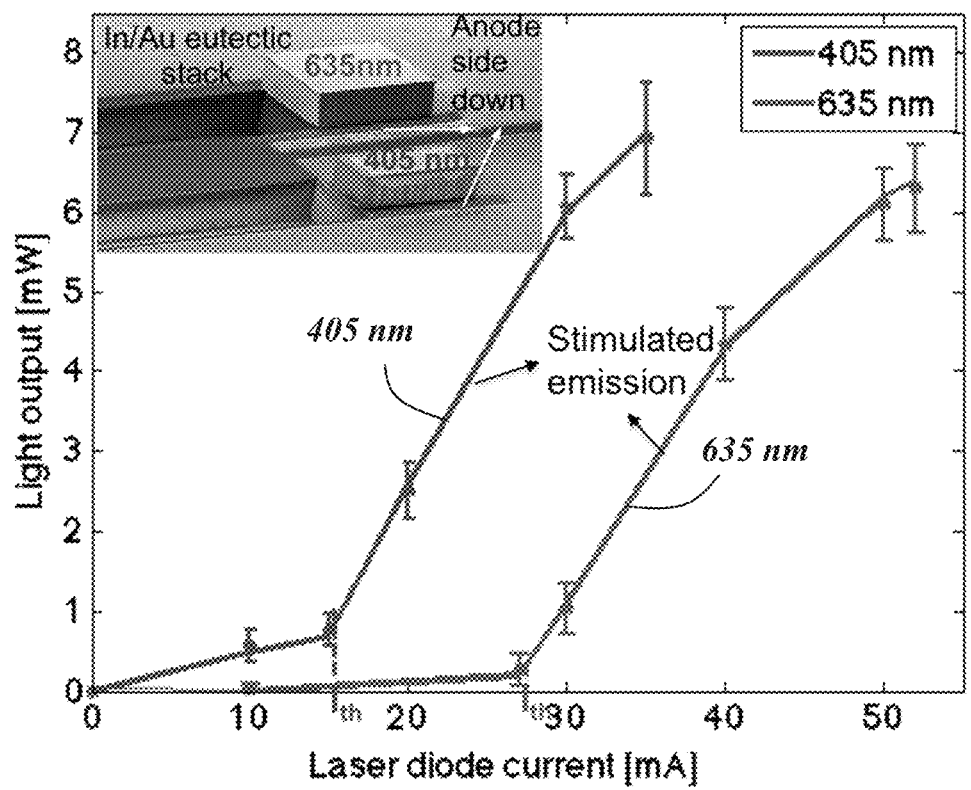
FIG. 11 is a graph illustrating light output-current (L-I) characteristics for one embodiment of epi-side down flip-chipped 405 nm and 635 nm ILDs with an inset showing an SEM image of flip-chip bonded ILDs.

As illustrated in FIG. 11, a wall-plug efficiency of 4.48% was achieved for a 405 nm packaged ILD. A wall-plug efficiency of 5.49% for a 635 nm packaged ILD was also achieved. The effectiveness of a light source assembly can be evaluated from its wall-plug efficiency or radiant flux. For ILDs, the wall-plug efficiency is the efficiency at which the diode assembly converts input electrical power into output optical power. In another example (not pictured), a wall-plug efficiency of 11.8% was achieved for a 405 nm packaged ILD. A wall-plug efficiency of 9.4% for a 635 nm packaged ILD was also achieved. In both embodiments, an epi-down, flux-less In—Au eutectic bonding configuration was used. The measured diode efficiency was in agreement with expectations—more than a 20% improvement in optical power and a 30% reduction in junction temperature and thermal resistance in epi-down mounted lasers in comparison to epi-up mounted lasers.

Optical loss may be quantified in each part of the system separately. For example, optical loss may include (1) coupling loss at the ILD-GRIN and GRIN-waveguide junctions; (2) radiation loss in the bends and corners of the optical mixer; and (3) propagation losses through the waveguide. Measurement using the direct cut-back method can be used to evaluate propagation loss per unit length of a straight waveguide, calculated as 0.5 dB/mm. The coupling (including Fresnel) loss between the GRIN lens and waveguide, including back reflection at the tip or emitting site of the waveguide was 1.76 dB. The coupling loss from ILD to GRIN output was separately estimated as 0.5±0.1 dB (mean±s.d., N=5) by comparing optical power at ILD (635 nm) and ILD-GRIN outputs. Radiation losses from straight channel waveguides are generally negligible for well-confined modes but may increase in waveguide bends. In one embodiment, the mixer geometry has two bends per light path, and radiation losses of 1.4±0.3 dB (mean±s.d., N=5) were measured when coupled to 635 nm ILD source. The summed losses of all sources measured for 635 nm light during bench testing was 7.18±0.22 dB for the complete waveguide length (7.04 mm). Packaged devices may have higher optical loss than estimated values from experimental devices, which may be due to misalignment in the micro assembly of optical components on a common substrate PCB in the packaged devices. Nevertheless, the experimental range of total optical loss of about 9.2-12.8 dB (with about 5.2-12% coupling efficiency) is high for diode-coupled optoelectrodes as compared with prior art devices. Previous work reported about a 30 dB loss for 650 nm wavelength and 26 dB for 465 nm wavelength, to cite a few examples. In another example, there was a 13 dB loss for 639 nm wavelength, but while one embodiment of the present optoelectrode had comparable optical losses for a single wavelengths, the present optoelectrode had a high-power diode-pumped solid-state (DPSS) based system. Further, one embodiment of the present optoelectrode, when coupled to a 6 mW ILD, had an average output intensity of 1928 mW/mm$^2$ (405 µW output power for 405 nm) and 2905 mW/mm$^2$ (610 µW for 635 nm) at the optical emission site.

Light propagation of the assembled optoelectrodes may also be evaluated. The target light intensity threshold for neural activation is typically 2 mW/mm$^2$ for Channelrhodopsin (ChR2) at 405 nm stimulation wavelength and 10 mW/mm$^2$ for Halorhodopsin (NpHR) at 635 nm stimulation wavelength in optogenetic studies. This target was surpassed during testing, measuring a maximum optical irradiance of 10476 mW/mm$^2$ with a 12.2% efficiency for 405 nm and 690 mW/mm$^2$ with a 5.4% efficiency for 635 nm at the maximum diode current ratings. Using Zemax optical modeling, alignment tolerances were simulated for ILDs, GRIN lenses, and a waveguide in detail. A GRIN lens misalignment of up to +/−25 μm may be tolerated with only 10% optical loss in all three axes, and the measurements generally agree with the simulations. Experimentally obtained light intensities- 10476 mW/mm² for 405 nm and 690 mW/mm² for 635 nm—were sufficient to optically stimulate local populations of genetically targeted neurons. Even with GRIN lens misalignment, relatively normalized output power of 90%, 95%, and 70% can be achieved within a tolerance of about +/−25 μm in the X and Y axes and about 10 μm in the Z axis, respectively. The ILD-GRIN coupling junction is typically the most tolerant of misalignment errors. In one example, the Y axis was the most sensitive to misalignment, where tolerance is dictated by the height of the waveguide core. In order to help accurately control the vertical GRIN-waveguide alignment, the emission point of an ILD can be aligned to the center of a waveguide cross-section by selecting the precise height of the probe jig. Since the jig is typically easily replaceable, the GRIN lens can be reliably and reproducibly positioned between the ILD and the waveguide.

Figure 12:
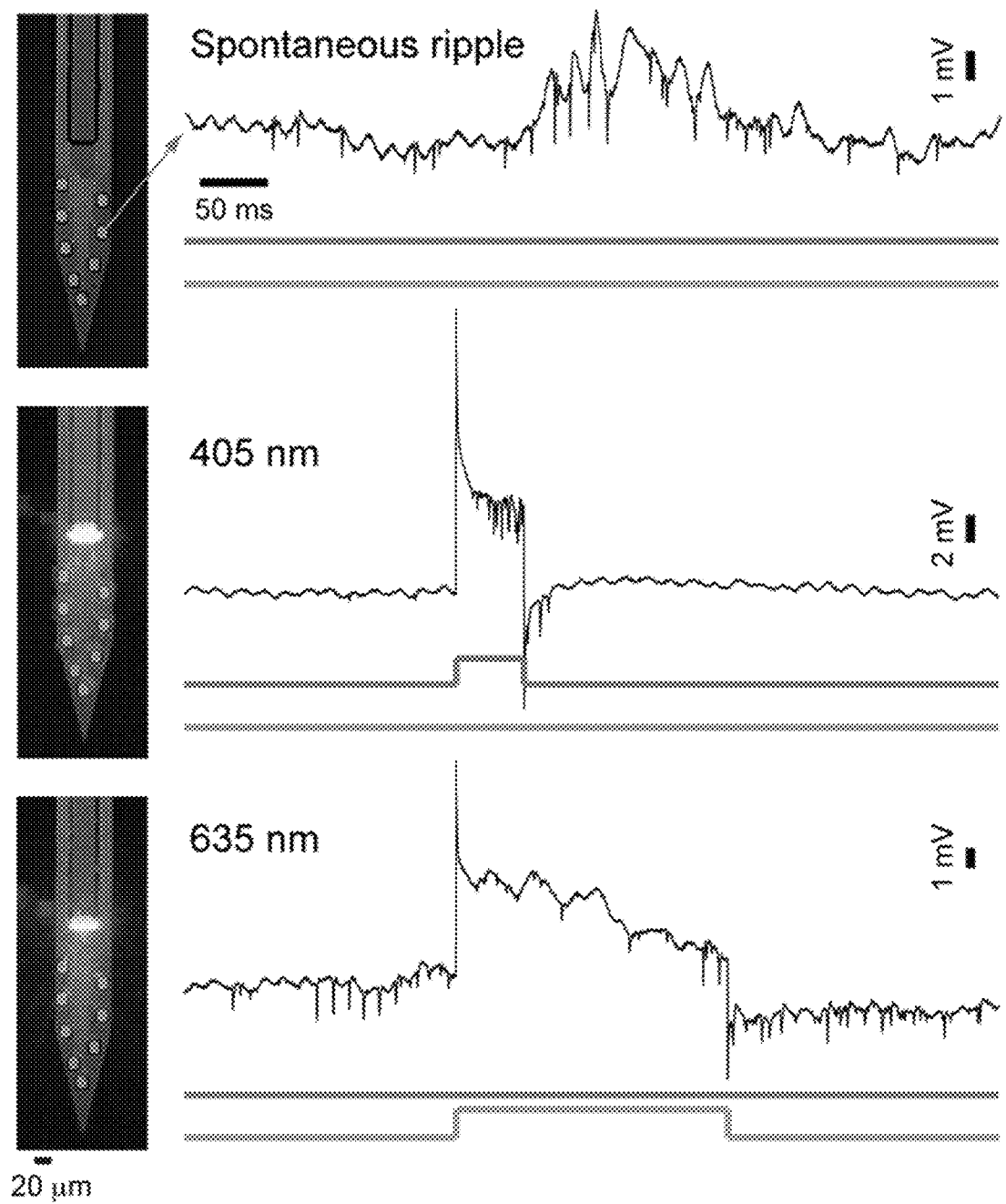
FIG. 12 shows wide-band traces recorded from the CA1 pyramidal cell layer of a urethane-anesthetized mouse when stimulated with one embodiment of an optoelectrode.
Figure 13:
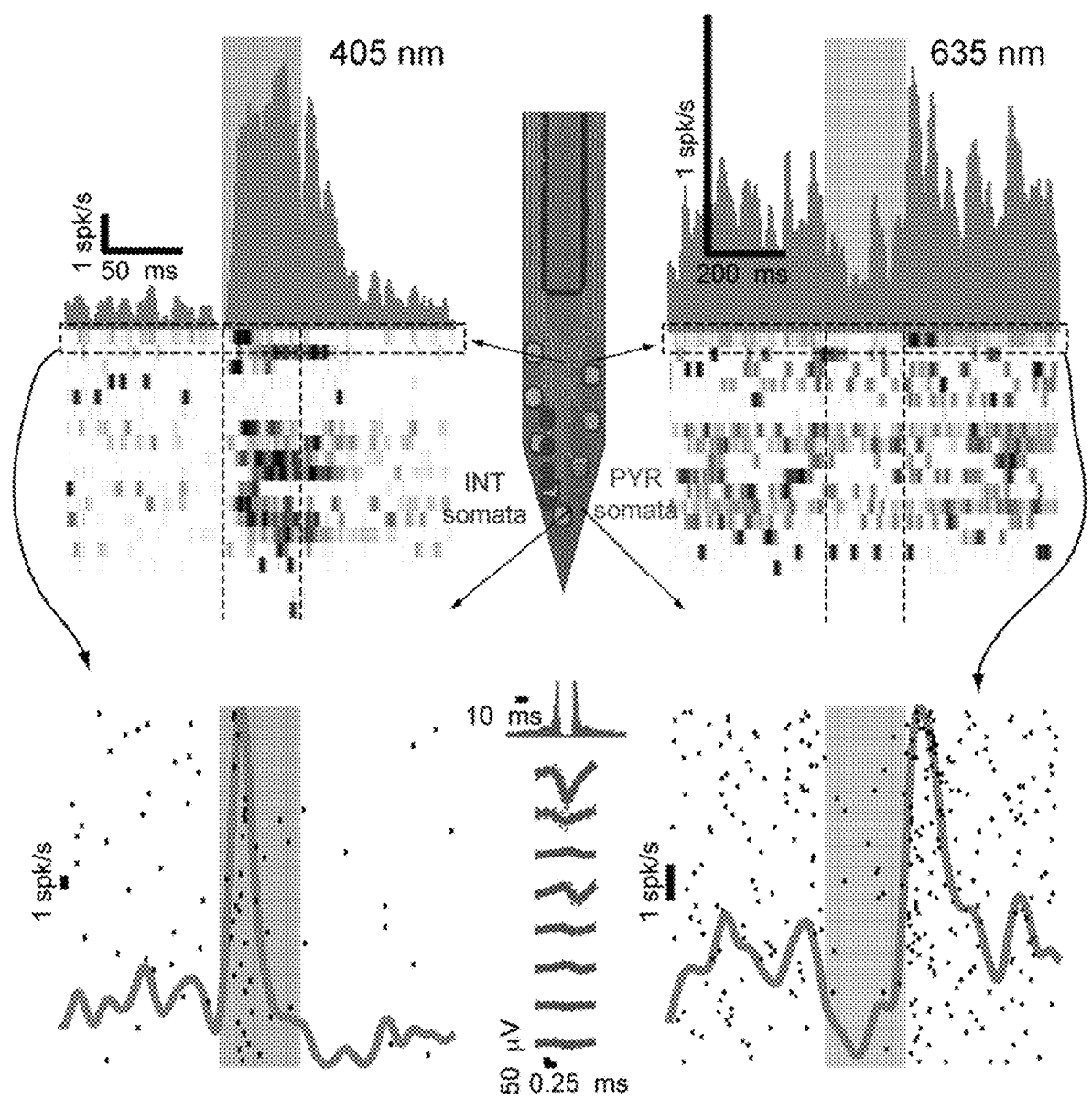
FIG. 13 shows spiking activity and raster plots for pyramidal cells recorded during the stimulation illustrated in FIG. 12.
Figure 14:
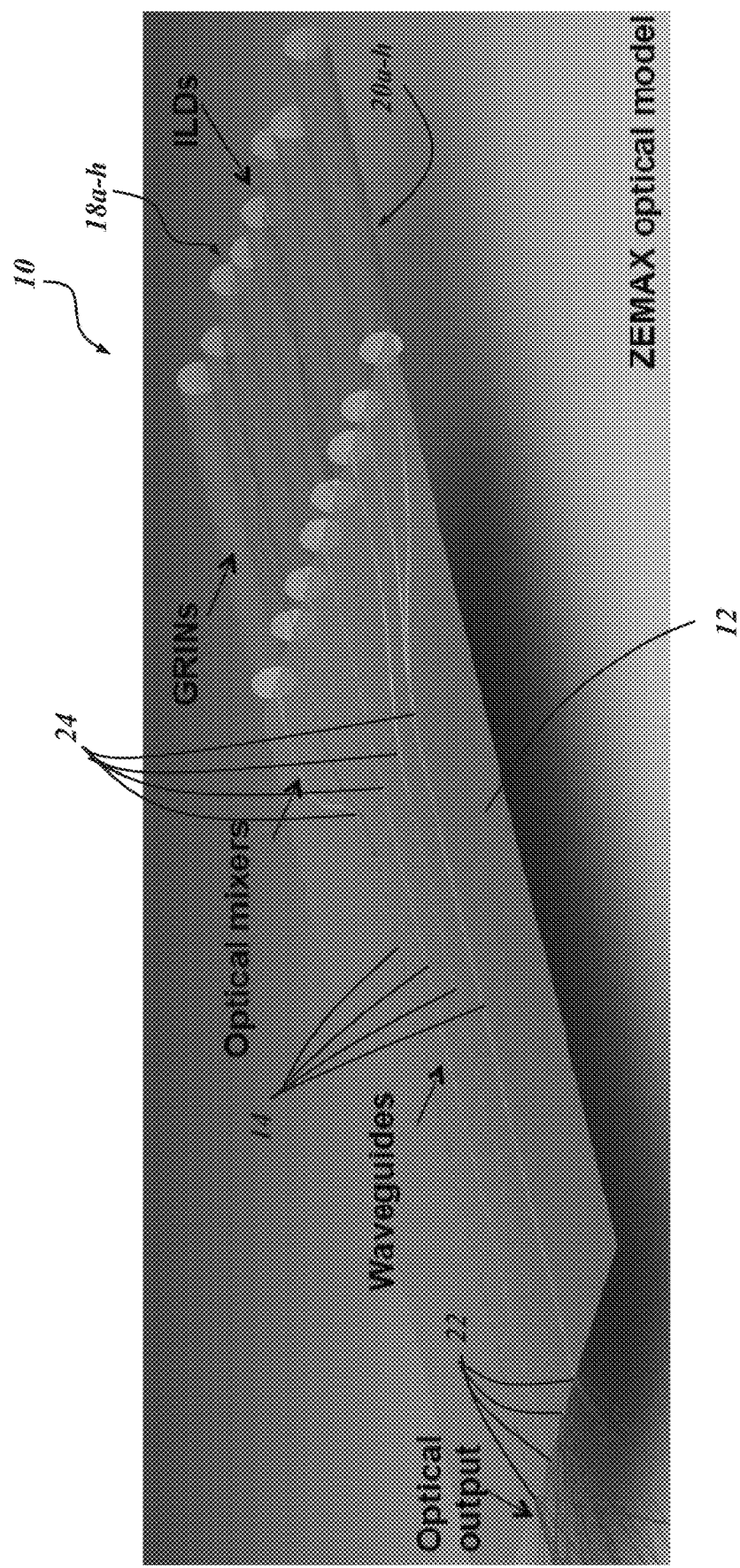
FIG. 14 is a Zemax optical model of another embodiment of a high-density fiberless multicolor optoelectrode.

FIGS. 12 and 13 illustrate in vivo electrophysiological results obtained with an embodiment of the optoelectrode 10. In this particular embodiment, the optoelectrode included an 8-site dual-ILD silicon probe. The optoelectrode was inserted into the CA1 pyramidal cell layer of urethane-anesthetized mice. As shown at the top of FIG. 12, spontaneous neural activity, including high-frequency ripple oscillations and multi-neuronal spiking was observed on all 8 channels. As shown in the middle of FIG. 12, when trains of 405 nm light pulses (50 ms, 1 pulse/s, 10 pulses/train; 30 mA, 100 μW at the waveguide tip) were applied, two features were evident. First, the recorded pyramidal cells (PYR) increased their spiking probability, consistent with ChR2 expression driven by the CaMKII-Cre driver in these animals. Second, the local field potential (LFP) exhibited stimulus-locked transient (onset and offset) and stimulation artifacts. These artifacts are comprised of a fast transient and DC offset with an asymptotic attenuation, features which are consistent with capacitive effects. As shown in the bottom of FIG. 12, when the trains of 635 nm light pulses (200 ms, 1 pulse/s, 10 pulses/train; 40 mA, 370 μW at the waveguide tip) were applied through the same waveguide without moving the probe, the same cells reduced their spiking rate. The LFP exhibited similar stimulus-locked transient (onset and offset) and artifacts. Similar artifacts were observed in a wild-type mouse that did not express any opsins and during sham recordings in PBS (data not shown).

With reference to FIG. 13, the cell-specific effect of light on a group of PYR (n=19) recorded simultaneously from CA1 was quantified. The inset in FIG. 13 shows the relative location of PYR and interneuron [INT] somata. Each cell was assessed for spike rate during the 405 nm light pulse, compared to baseline spiking rate (in the lack of any light). Most (11/19; 58%) of the cells increased their spike rate ($p<0.05$, Poisson test), with a median gain (spike rate during light divided by baseline rate) of 15.1, as shown in the top left of FIG. 13. Using the same approach, the same cells were also assessed for spike modulation during 635 nm light: 4/19 cells (21%) exhibited a consistent rate decrease ($p<0.05$, Poisson test), with a median gain of 0.11, as shown in the top right of FIG. 13. One PYR, the one closest to the waveguide (estimated distance from waveguide tip to soma, 75 μm), as shown in the bottom to graphs of FIG. 13, exhibited both consistent rate increase and rate decrease ($p<0.001$ for both).

Figure 15:
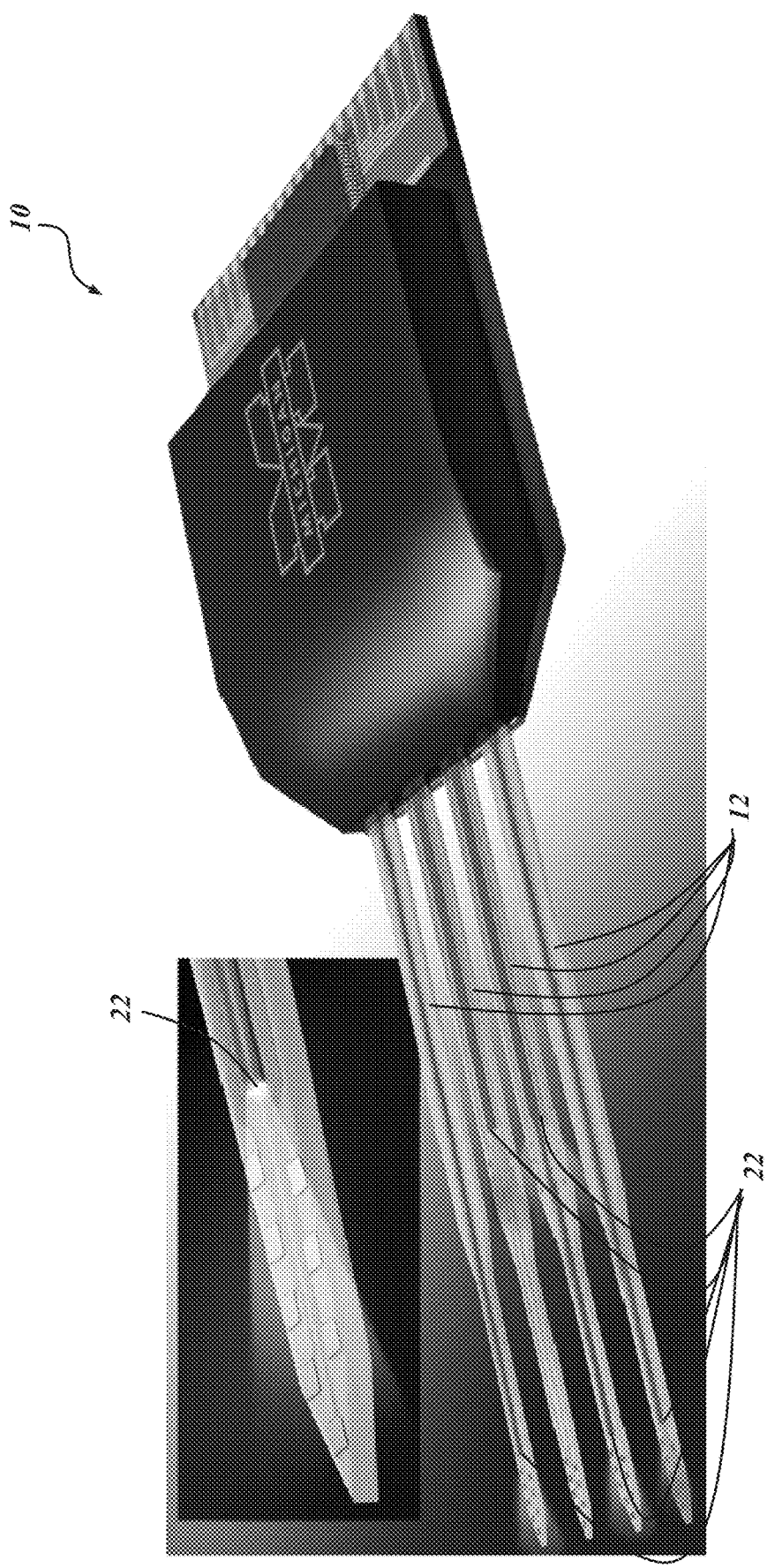
FIG. 15 is a schematic perspective view of another embodiment of a high-density fiberless multicolor optoelectrode
Figure 16:
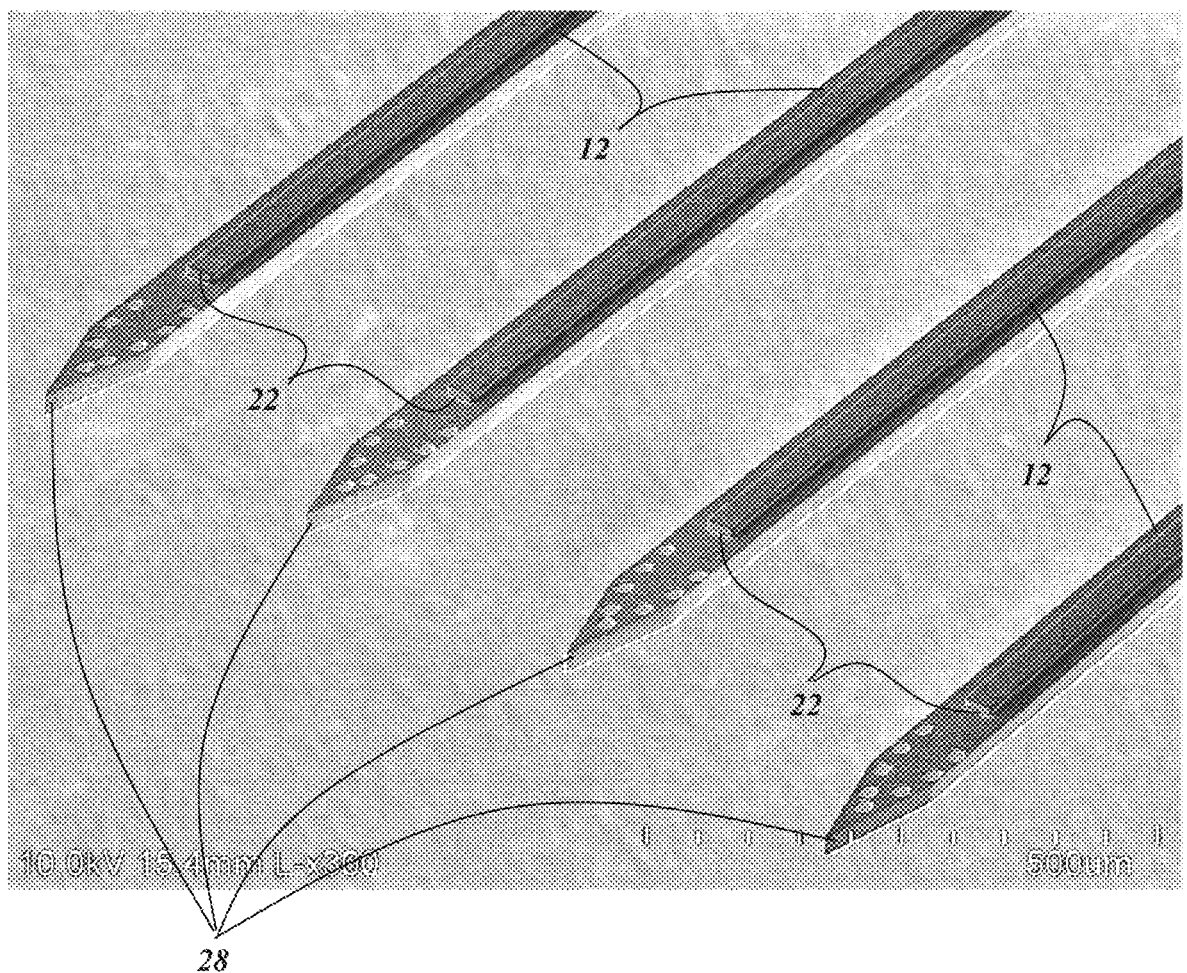
FIG. 16 is an image of an end of an optoelectrode that includes four probe shanks.
Figure 17:
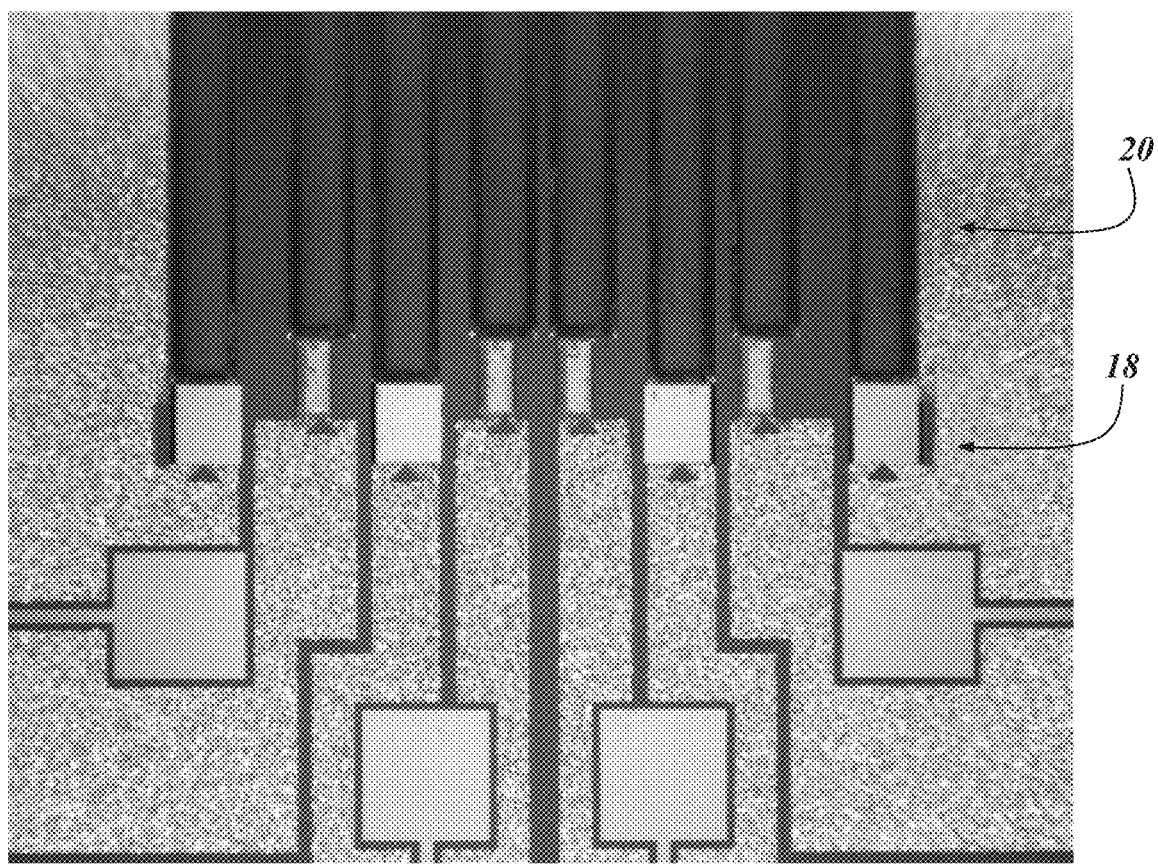
FIG. 17 is an image showing 8 assembled light sources on a source module.

FIGS. 14-17 illustrate other embodiments of optoelectrodes 10. The optoelectrode 10 of FIG. 14 includes eight ILDs 18a-18h and an associated eight GRINs 20a-20h, with four optical mixers 24 that each combine the light exiting a different pair of the GRINs for transmission by one of four light guides to four different optical ports. With reference to FIG. 15, an optoelectrode 10 is shown having four separate probe shanks 12, and varying optical emission ports 22. It should be understood that light of different wavelengths can be provided at one or more optical emission ports, via one or more waveguides on one or more probe shanks. In one example embodiment, an optoelectrode can have three light sources providing red, green, and violet light respectively, which are the three light colors that typically stimulate neurons. Light sources providing different, single-wavelength light may be used, or sources having more than one wavelength may be used. Multiple light sources that produce light having the same wavelength may also be included in one optoelectrode. FIG. 16 shows an enlarged view of the tips 28 of four separate probe shanks 22. FIG. 17 shows an embodiment of an optoelectrode which includes eight light sources 18 coupled via eight lenses 20.

The waveguide may further include an optical multiplexer between the GRIN lens and the waveguide that may be used to increase the number of independent light channels without increasing the number of light sources. For example, a Mach Zendher interferometer having electrical or thermal actuation may be used to create a 1×2 or 2×4 or 2×n multiplexer having more independent light channels than the number of independent light sources. The multiplexer "chip" may be an additional component or integrated component that butt couples its waveguide output to the neural probe waveguide input.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. An optoelectrode, comprising:
   a probe shank;
   a light guide positioned on the probe shank;
   a source module;
   a light source attached to the source module; and
   a gradient-index (GRIN) lens, wherein the GRIN lens has
      a flat coupling end and is optically coupled between the light source and the light guide such that light from the light source can be directed by the GRIN lens to the light guide and transmitted through the light guide to an optical emission port of the probe shank, wherein the coupling between the light source and the GRIN lens is an end-fire coupling at the flat coupling end.

2. A method of making the optoelectrode of claim 1, comprising the steps of:
   assembling the light guide on the probe shank;
   assembling the light source on the source module; and
   coupling the light source to the light guide using the gradient index (GRIN) lens.

3. The method of claim 2, wherein the light source is a side-emitting injection laser diode (ILD) and the light source assembling step includes die bonding the side-emitting ILD to the source module.

4. The method of claim 3, wherein the die-bonding step includes attaching the side-emitting injection laser diode (ILD) in an epi-down configuration.

5. The method of claim 3, wherein the light guide is a waveguide, and the coupling step includes coupling the gradient index (GRIN) lens such that one end of the GRIN lens faces toward an emission point of the side-emitting injection laser diode (ILD) forming an ILD-GRIN assembly, and the ILD-GRIN assembly is focused into an input arm of a waveguide mixer at a distal end of the waveguide.

6. The method of claim 2, wherein the coupling step includes placing the lens in a groove positioned in front of the light source.

7. The optoelectrode of claim 1, wherein the light source is a laser diode, a light emitting diode, or a fibered source.

8. The optoelectrode of claim 7, wherein the light source is a side-emitting injection laser diode (ILD) that is attached to the source module in an epi-down bonding configuration.

9. The optoelectrode of claim 1, wherein the light guide is a patterned waveguide.

10. The optoelectrode of claim 1, further comprising a plurality of light sources and an optical mixer, wherein at least two of the plurality of light sources provide light of differing wavelengths.

11. The optoelectrode of claim 1, further comprising an optical multiplexer between the GRIN lens and the waveguide, wherein the optical multiplexer provides for a greater number of independent light channels than light sources.

12. The optoelectrode of claim 1, further comprising a plurality of light sources, wherein the light guide includes an optical mixer that is configured to facilitate the selective transmission of light from each light source of the plurality of light sources.

13. The optoelectrode of claim 1, wherein the source module includes a heat sink configured to facilitate heat dissipation from the light source away from the probe shank.

14. The optoelectrode of claim 1, further comprising a plurality of probe shanks each having an optical emission port, wherein at least two optical emission ports are located at different positions along a length of their respective probe shank.

15. An optoelectrode, comprising:
   a probe shank;
   a light guide positioned on the probe shank;
   a source module;
   a light source attached to the source module; and
   a gradient-index (GRIN) lens, wherein the GRIN lens is optically coupled between the light source and the light guide such that light from the light source can be directed by the GRIN lens to the light guide and transmitted through the light guide to an optical emission port of the probe shank, wherein the coupling between the light source and the GRIN lens is an end-fire coupling, wherein the mechanical length of the GRIN lens corresponds with the wavelength of the light emitted from the light source.

16. The optoelectrode of claim 15, wherein the mechanical length of the gradient-index (GRIN) lens corresponds to a proportion of a wavelength of the light emitted from the light source.

17. An optoelectrode, comprising:
   a waveguide ending at an optical emission port configured to be inserted into a tissue sample;
   a light source, wherein the light source is a side-emitting injection laser diode (ILD); and
   a gradient index (GRIN) lens that is optically coupled between the light source and the waveguide such that light from the light source can be directed by the lens to the waveguide and transmitted through the waveguide to the optical emission port.

18. The optoelectrode of claim 17, wherein the numerical aperture (N.A.) of the waveguide is equal to or higher than the N.A. of the gradient index (GRIN) lens.

* * * * *